United States Patent
Schneider et al.

(10) Patent No.: US 9,297,739 B2
(45) Date of Patent: Mar. 29, 2016

(54) METHOD AND A DEVICE FOR ESTIMATING A POROSITY RATIO OF A SAMPLE OF MATERIAL FROM AT LEAST ONE GRAY-SCALE CODED IMAGE

(71) Applicant: SNECMA, Paris (FR)

(72) Inventors: Julien Schneider, Corbeil-Essonnes (FR); Benedicte Marie Le Borgne, Orsay (FR)

(73) Assignee: SNECMA, Paris (FR)

( * ) Notice: Subject to any disclaimer, the term of this patent is extended or adjusted under 35 U.S.C. 154(b) by 0 days.

(21) Appl. No.: 14/353,573

(22) PCT Filed: Nov. 6, 2012

(86) PCT No.: PCT/FR2012/052558
§ 371 (c)(1),
(2) Date: Apr. 23, 2014

(87) PCT Pub. No.: WO2013/068687
PCT Pub. Date: May 16, 2013

(65) Prior Publication Data
US 2014/0286564 A1    Sep. 25, 2014

(30) Foreign Application Priority Data
Nov. 9, 2011    (FR) ...................................... 11 60196

(51) Int. Cl.
*G01N 15/08*    (2006.01)
*G06T 7/00*    (2006.01)

(52) U.S. Cl.
CPC ............ *G01N 15/088* (2013.01); *G06T 7/0002* (2013.01); *G06T 7/0004* (2013.01); *G01N 2015/0846* (2013.01); *G06T 2207/10072* (2013.01); *G06T 2207/10081* (2013.01); *G06T 2207/10116* (2013.01); *G06T 2207/30108* (2013.01)

(58) Field of Classification Search
USPC .......................................................... 382/141
See application file for complete search history.

(56) References Cited

U.S. PATENT DOCUMENTS

2014/0270468 A1* 9/2014 Tam et al. ..................... 382/144

OTHER PUBLICATIONS

Farber, Leon. "Use of X-Ray Tomography to Study the Porosity and Morphology of Granuales." Powder Technology (Jan. 28, 2003): 57-63. www.elsevier.com/locate/powtec.*
Alien Research. "Goldilocks Condition." Oct. 2, 2011. Accessed May 14, 2015. http://alienresearch.wikia.com/wiki/Goldilocks_conditions.*

(Continued)

*Primary Examiner* — Utpal Shah
*Assistant Examiner* — Kate R Duffy
(74) *Attorney, Agent, or Firm* — Oblon, McClelland, Maier & Neustadt, L.L.P.

(57) ABSTRACT

A method and device for estimating a porosity ratio of a sample of material from at least one gray-scale coded image. The method includes: evaluating an intermediate ratio of a sample for each value of a plurality of gray-scale threshold values lying between two determined limit values, the intermediate ratio being equal to a ratio of a number of pixels of the at least one image having a gray-scale value bounded by the threshold value to a total number of pixels of the at least one image; and estimating the porosity ratio of the sample by analyzing variations in the intermediate ratio as a function of the threshold value.

9 Claims, 2 Drawing Sheets

(56) References Cited

OTHER PUBLICATIONS

Yohann Ledru, "Etude de la porosite dans les materiaux composites stratifies aeronautiques" pp. 115-151 (Total 43 Pages), XP002674462, (Dec. 2009).

Christe, et al., "An X-ray computed tomography-based index to characterize the quality of cataclastic carbonate rock samples", Engineering Geology, vol. 117, No. 3-4, pp. 180-188, XP027599311, (Feb. 2011).

Jones et al., "Application of invariant grey scale features for analysis of porous minerals", Micron, vol. 38, No. 1, pp. 40-48, XP005710884, (Jan. 2007).

International Search Report Issued Jan. 2, 2013 in PCT/FR12/52558, Filed Nov. 6, 2012.

\* cited by examiner

METHOD AND A DEVICE FOR ESTIMATING A POROSITY RATIO OF A SAMPLE OF MATERIAL FROM AT LEAST ONE GRAY-SCALE CODED IMAGE

BACKGROUND OF THE INVENTION

The invention relates to the general field of materials.

More particularly, it relates to estimating the porosity ratio of a material (ratio per unit area or per unit volume), such as for example a composite material. In known manner, the porosity of a material characterizes the pore content of the material, i.e. its content of interstitial voids that may optionally be interconnected.

The invention thus has a preferred but non-limiting application in the field of aviation.

It is nowadays common practice to use primary structures made of composite material in the production of aircraft (e.g. turbojet blades, etc.). Such structures are subjected to strict quality control during which the volume porosity ratio of the composite materials is monitored closely. The presence of porosities in the material can be detrimental to good mechanical strength, so the purpose of the inspection is to make sure that the volume porosity ratio of the material does not exceed a predefined limit value.

In order to determine the porosity ratio of a composite material, it is known to have recourse to a technique of degrading or dissolving the matrix of the material (e.g. chemically by acid attack or by calcination).

In that technique, readings are taken of the weights of a sample of composite material before and after dissolving its matrix. On the basis of knowledge of the densities of the fibers and of the matrix of the material, these weight readings make it possible to calculate easily the volume porosity ratio of the composite material.

Nevertheless, that technique presents a certain number of drawbacks.

Firstly, it depends strongly on the accuracy with which the weights are read and also on the knowledge of the densities of the fibers and of the matrix of the composite material.

Furthermore, that technique is destructive: it relies on totally dissolving the matrix of the composite material. Unfortunately, not only does such dissolution take a long time (several hours), but there also remains doubt as to whether the matrix has been dissolved in full. Furthermore, the presence of foreign particles or ingredients in the material, such as for example inclusions of metal or of glass fiber, have a major effect on calculating the volume porosity ratio.

Finally, that technique is difficult to apply industrially to materials made of metal or to composite materials having a matrix that is made of ceramic or of metal.

The document by Y. Ledru et al. entitled "*Quantification 2-D et 3-D de la porosité par analyse d'images dans les matériaux composites stratifiés aéronautiques*" [2D and 3D quantification of porosity by analyzing images of stratified aviation composite materials], JNC 16, Toulouse, 2009, proposes a technique of estimating the porosity ratio of a composite material in non-destructive manner on the basis of analyzing images that are gray-scale coded.

More particularly, it proposes isolating in said images pixels that correspond to porosities and pixels that correspond to matter. The volume porosity ratio of the composite material is then deduced from the number of pixels corresponding to porosities as isolated in this way.

Nevertheless, that technique relies on an operator setting a gray-scale value threshold for distinguishing pixels. Operator action makes the analysis undertaken in that document subjective and therefore difficult to verify or to perform reproducibly.

OBJECT AND SUMMARY OF THE INVENTION

The present invention makes it possible to remedy that drawback in particular by proposing a method of estimating a porosity ratio of a sample of material from at least one gray-scale coded image representing the sample, the method comprising:
  a step of evaluating an intermediate ratio for each value of a plurality of gray-scale threshold values lying between two determined limit values, this intermediate ratio being equal to the ratio of the number of pixels of said at least one image having a gray-scale value bounded by the threshold value to the total number of pixels in said at least one image; and
  a step of estimating the porosity ratio of the sample by analyzing variations in the intermediate ratio as a function of threshold value.

Correspondingly, the invention also provides a device for estimating a porosity ratio of a sample of material from at least one gray-scale coded image representing the sample, the device comprising:
  at least means for evaluating an intermediate ratio for each value of a plurality of gray-scale threshold values lying between two determined limit values, the intermediate ratio being equal to the ratio of the number of pixels of said at least one image having a gray-scale value bounded by said threshold value to the total number of pixels of said at least one image; and
  means for estimating the porosity ratio of the sample by analyzing variations in the intermediate ratio as a function of threshold value.

The term "pixels having a gray-scale value bounded by a threshold value" is used in the invention to mean pixels having respective gray-scale values all situated on the same side of the threshold value, i.e. bounded either on the right by the threshold value or else bounded on the left. Which one of these sides is selected depends on the way in which porosities and/or matter is/are represented in the gray-scale coded images, i.e. on whether paler gray-scale values in the images correspond to porosities or to matter.

In other words, the intermediate ratio evaluated in accordance with the invention is equal:
  to the proportion of pixels in the images having a gray-scale value less than the threshold value if the gray-scale values representing porosities of the sample in the images have lower values than the gray-scale values representing matter; or
  to the proportion of pixels in the images having a gray-scale value greater than the threshold value if the gray-scale values representing porosities of the sample in the images have greater values than the gray-scale values representing matter.

The invention thus proposes a method that is non-destructive, simple, and accurate, for the purpose of determining the area porosity ratio or per unit volume of a material.

It should be observed that the invention applies advantageously to material of any type, and in particular to composite materials. The invention also makes it possible to determine the porosity ratio of materials for which it is very difficult to make use of conventional methods such as methods of dissolving in acid.

The method of the invention may be fully automated and thus avoid any operator intervention. Thus, not only are the results that are obtained reproducible and accurate, but using the method of the invention also achieves a non-negligible saving in time compared with dissolving techniques (a saving better than a factor of 3 for a sample having dimensions 10 millimeters (mm)×10 mm×10 mm, including the time required to acquire the gray-scale coded images.

It should also be observed that this technique makes it possible to process samples of larger size than the above-described dissolving techniques.

The gray-scale coded images under consideration are preferably images representing the sample in three dimensions. These images may be obtained by tomography, for example. The pixels are then three-dimensional pixels (by way of example each pixel associates a gray-scale value with the three-dimensional coordinates of a point in the image), which pixels are also known as voxels (short for "volume pixels"). The estimation method of the invention thus makes it possible to obtain a volume porosity ratio directly. As a result, in order to obtain the volume porosity ratio of a sample there is thus no need to convert from an area ratio: the estimate that is obtained is consequently more accurate.

The curve representing variations in the intermediate ratio as a function of threshold value is very characteristic: it presents two substantially linear portions with very distinct slopes on either side of a "break" point. Advantageously, the inventors have observed (and verified using a dissolving technique) that the break point reflecting the change in the slope of the curve gives an accurate estimate of the volume porosity ratio of the material under test.

Thus, in a particular implementation, the step of estimating the porosity ratio comprises:
  on a curve representing variations in the intermediate ratio as a function of threshold value, identifying a point reflecting a significant change in slope of the curve; and
  estimating the porosity ratio of the sample from the ordinate value of this point.

A change of slope is said to be "significant" when it marks a clear break in the slopes of the curve, i.e. the curve has slopes on either side of this point that are very different (or in equivalent manner, the ratio of the slopes on either side of the point is greater than a predefined threshold).

Thus, by way of example, in order to detect the point, attention is given to the second derivative of the curve: the point reflecting a significant change of slope in the curve corresponds to a maximum of the second derivative.

In a variant, it is ensured that a change in slope is significant by verifying that the ratio of the slopes on either side of the point is greater than a predetermined threshold.

In an implementation, the limit values are determined from information contained in at least one said gray-scale coded image. For example, the limit values may be extracted automatically by observing the values taken by the gray-scale values in the image.

In another implementation, prior to the evaluation step, the method also includes a step of classifying the gray-scale values of said at least one gray-scale coded image in increasing or decreasing order.

This step makes it easier to process the images and to count pixels having identical gray-scale values. Furthermore, as a result of this step there is no need to analyze all of the pixels of the images: it can suffice to limit analysis to pixels having gray-scale values lying between the two limit values of the threshold values.

In a particular implementation, the various steps of the method of estimating the porosity ratio of a sample of material are determined by computer program instructions.

Consequently, the invention also provides a computer program on a data medium, the program being suitable for being performed in an estimator device or more generally in a computer, the program including instructions adapted to perform steps of an estimation method as described above.

The program may use any programming language, and be in the form of source code, object code, or of code intermediate between source code and object code, such as in a partially compiled form, or in any other desirable form.

The invention also provides a computer readable data medium including computer program instructions as mentioned above.

The data medium may be any entity or device capable of storing the program. For example, the medium may comprise storage means such as a read only memory (ROM), e.g. a compact disk (CD) ROM, or a microelectronic circuit ROM, or indeed magnetic recording means, e.g. a floppy disk or a hard disk.

Furthermore, the data medium may be a transmissible medium such as an electrical or optical signal, which may be conveyed via an electrical or optical cable, by radio, or by other means. The program of the invention may in particular be downloaded from an Internet type network.

Alternatively, the data medium may be an integrated circuit in which the program is incorporated, the circuit being adapted to execute or to be used in the execution of the method in question.

In other implementations, it is possible to envisage that the method and/or the device for estimating a porosity ratio in accordance with the invention presents some or all of the above-mentioned characteristics in combination.

BRIEF DESCRIPTION OF THE DRAWINGS

Other characteristics and advantages of the present invention appear from the following description given with reference to the accompanying drawings which show an implementation having no limiting character. In the figures.

DETAILED DESCRIPTION OF THE INVENTION

Figure 1:
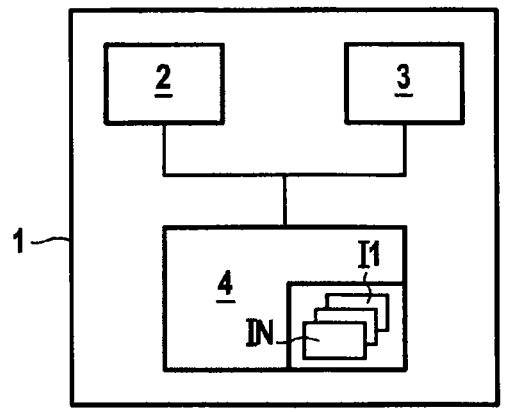
FIG. 1 shows a particular embodiment of a device for estimating the porosity ratio of a material in accordance with the invention, the device being shown in its environment.

FIG. 1 shows a particular embodiment of a device 1 of the invention for estimating a porosity ratio $\tau_E$ of a sample E of material in accordance with the invention, the device being shown in its environment.

In the presently-described example, the sample E is a sample of composite material with an organic, ceramic, or metal matrix. Nevertheless, the invention is not limited to composite materials and it may be applied to samples of any material, such as for example a sample of a homogeneous material (e.g. a metal, a plastics material, etc.).

In accordance with the invention, the estimation device 1 is suitable for estimating the porosity ratio of the sample E from one or more images I1, I2, . . . , IN (N≥1, e.g. N=1000), showing the sample E and coded on a gray-scale. In the presently described example, a void is represented in the images I1, I2, . . . , IN by gray-scale values that are "low" compared with gray-scale values representing matter: in other words, in the images I1, I2, . . . , IN, the gray-scale values representing porosities in the sample E are lighter than the gray-scale values representing matter.

Naturally, this assumption is not limiting, and the invention is equally applicable to images in which the gray-scale values representing porosities in the sample E are darker than the gray-scale values representing matter.

The number N of images taken into consideration for estimating the porosity ratio may depend on various parameters, such as in particular whether porosities are present in the images in large numbers or not at all (e.g. if an image shows a large number of porosities in the sample of material, that one image may be sufficient to estimate the porosity ratio of the sample reliably in accordance with the invention), with a compromise between the accuracy of the estimate and the required resources in terms of calculation power and/or memory needed for making the estimate, etc.

In the presently described implementation, the images I1, . . . , IN show the sample E in three dimensions (i.e. in the form of a plurality of voxels, i.e. three-dimensional pixels), such that the porosity ratio estimated by the invention is a volume porosity ratio.

The images I1, I2, . . . , IN are obtained in this example by tomography, e.g. using X-rays. In known manner, X-ray tomography techniques make it possible to obtain a three-dimensional reconstruction of the item being processed by using X-rays. The quality of the tomographic images should be selected to be sufficient to make it possible to distinguish between matter and voids, which nowadays does not present any difficulty in practice given the technique used in tomography.

Nevertheless, these assumptions are not limiting.

The invention also makes it possible to estimate a porosity ratio from images showing the sample in two dimensions (in the form of a plurality of two-dimensional pixels). The resulting porosity ratio is then an area porosity ratio. This ratio may be converted into a volume porosity ratio, should that be necessary, in a manner that is known to the person skilled in the art. By way of example, a conversion technique is described in the above-mentioned document by Y. Ledru et al.

Thus, in the meaning of the invention, the term "pixel" covers both a two-dimensional pixel and a three-dimensional pixel (or "voxel"), depending on the type of gray-level coded image under consideration for estimating the porosity ratio.

Furthermore, the invention is not limited to images with a gray-scale value coding obtained with the help of tomographic techniques. Other techniques may be envisaged, such as for example, magnetic resonance imaging (MRI) techniques, providing the images obtained are of quality that is sufficiently good to distinguish voids from matter.

The estimation device 1 in this example has the hardware architecture of a computer. In particular it comprises a processor 2, random access memory (RAM) 3, and ROM 4, in known manner.

The ROM 4 of the estimation device 1 constitutes a storage medium in accordance with the invention that is readable by the processor 2 and that stores a computer program in accordance with the invention including instructions for executing steps of a method of the invention for estimating a porosity ratio, as described below with reference to FIG. 2.

Figure 2:
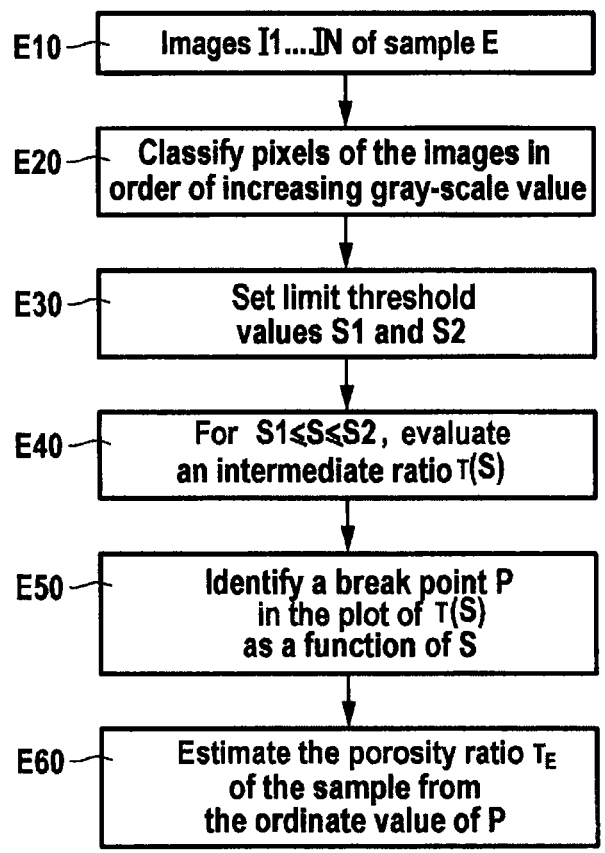
FIG. 2 is a flow chart showing the main steps of an estimation method in accordance with the invention in a particular implementation in which the method is performed by the device of FIG. 1.

FIG. 2 is a flow chart showing the main steps of a method of estimating a porosity ratio in accordance with the invention, in a particular implementation.

In the presently described example, the N images I1, I2, . . . , IN of the sample E presented with gray-scale value coding and showing the sample E in three dimensions are transmitted to the estimation device 1 (step E10).

These images are stored in the ROM 4 of the estimation device 1 in the form of files F1, . . . , FN, each file Fn (n=1, . . . , N) associating each 3D pixel (voxel) of the image In (as identified by its coordinates) with a gray-scale coded on k bits (e.g. k=16 bits, making it possible to code 65536 gray-scale values). For simplification in the description below, reference is made to the "pixels" of an image In, even though in the presently envisaged example they are voxels.

In the presently described implementation, the estimation device 1 creates a file F from the information contained in the files F1, . . . , FN, in which it lists the gray-scale values of all of the pixels shown in the images I1, . . . , IN. In addition, in this file, the gray-scale values are classified in increasing order with the help of a known sorting algorithm, in order to make them easier to process.

Naturally, this assumption is not limiting, and it is possible to envisage some other type of classification (or indeed no classification).

In parallel with this step, or following it, the estimation device 1 selects one of the files F1, . . . , FN and analyses the variations of gray-scale values along one or more rows of the image corresponding to the selected file (a row corresponds to pixels of constant ordinate value in the selected file).

The file selected by the estimation device 1 preferably includes at least one row passing through a porosity. By way of example, in order to identify such a file, in addition to considering the sample for which it is desired to determine the porosity ratio, consideration may also be given to a standard sample having a known porosity, and a file may be selected including a row that passes through that known porosity of the standard sample.

In a variant, the estimation device 1 selects a file at random or a predetermined file, e.g. the file F1, or indeed a file identified by an operator from among the files F1, . . . , FN, and including at least one row passing through a porosity.

Figure 3:
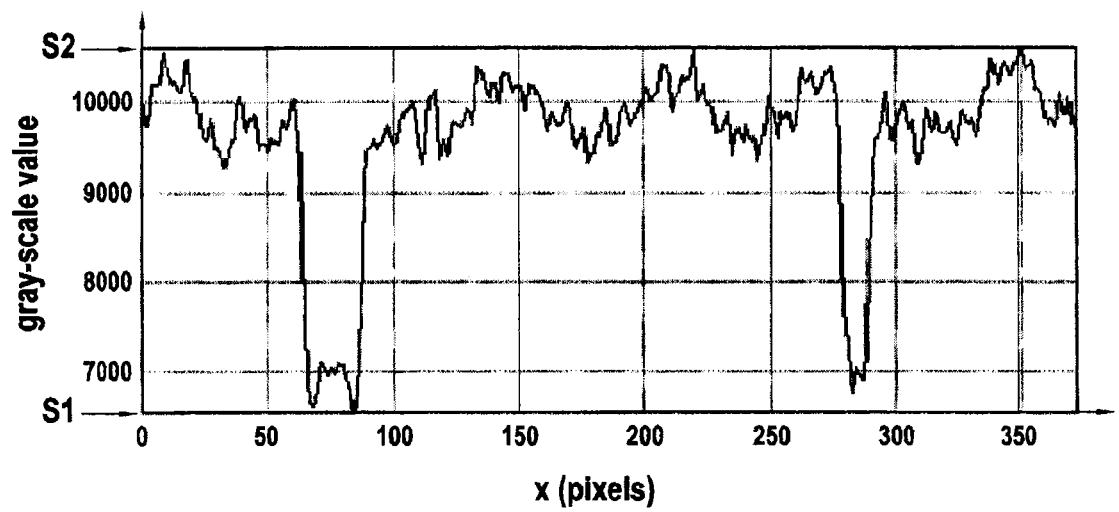
FIG. 3 is a diagram showing variations in gray-scale values in an image.

FIG. 3 shows an example of a curve representing variations in gray-scale value along an image row as selected in this way (where x represents the abscissa value of each pixel).

On the basis of an analysis of these variations, the device 1 extracts two gray-scale limit values S1 and S2 (step E30). These two limit values define a range of gray-scale values within which there lies the gray-scale threshold value that corresponds to the frontier between voids and matter, or in other words, and in this example, below which a pixel represents a porosity in the sample E (i.e. a void), and above which a pixel corresponds to matter.

In a variant, if the gray-scale values representing porosities in the images I1, I2, . . . , IN are greater than the gray-scale values representing matter, then the gray-scale threshold value corresponding to the boundary between voids and matter corresponds to the threshold above which a pixel is representative of a porosity in the sample E and below which a pixel corresponds to matter.

More precisely, in this example, S1 is selected as the minimum value taken by the gray-scale values along the row under consideration (i.e. S1≈6600), and S2 is selected as the maximum value taken by the gray-scale values (i.e. S2≈14,000) along this row.

Naturally, other values could be selected by the estimation device 1 for S1 and S2, such as for example S1=9000 and S2=14,000, given the general appearance of the curve 3.

Furthermore, in a variant, S1 and S2 may be extracted from variations in gray-scale value corresponding to a plurality of images, in particular for the purpose of confirming the values selected on one image.

In yet another variant implementation of the invention, the estimation device 1 determines as gray-scale limit values the two extreme values S1=0 and S2=$2^k$ for the gray-scale values that can be taken by the pixels in the image (i.e. in this example S2=65,536 for k equal to 16 bits).

The values S1 and S2 as set in this way constitute limit threshold values in the meaning of the invention.

The device 1 then initializes a threshold value S at S1 and evaluates an intermediate ratio τ(S) for the sample E of material (step E40) with the help of the following equation:

$$\tau(S) = A_{inf}/A_{tot}$$

where $A_{inf}$ designates the number of pixels representing the sample E and listed in the file F (i.e. in the set of images I1, . . . , IN) as having a gray-scale value below the threshold value S, and $A_{tot}$ designates the total number of pixels listed in the file F representing the sample E (i.e. the sum of the numbers of pixels in each of the images representing the sample E).

In a variant, if the gray-scale values in the images I1, I2, . . . , IN representing porosities are greater than the gray-scale values representing matter, then the number $A_{inf}$ designates the number of pixels listed in the file F as having a gray-scale value greater than the threshold value S.

It should be observed that since the gray-scale values of the pixels are classified in increasing order, it is easier to identify pixels having respective gray-scale values below the threshold S. Furthermore, and advantageously, there is no need to analyze the gray-scale values of all of the pixels stored in the file F in order to determine the numbers $A_{inf}$ and $A_{tot}$.

The value of the intermediate ratio τ(S) as obtained in this way is stored in the RAM 3 of the device 1 in association with the threshold value S.

Thereafter, the device 1 increments the value S by a predetermined increment value (i.e. S←S+incr), and reiterates evaluation of the intermediate ratio with this new threshold value, etc., up to the value S=S2.

In the presently described implementation, the increment incr is constant over the range of values [S1, S2]. In a variant, this increment may depend on the threshold values S taken into consideration. Thus, for example, with reference to FIG. 3, for threshold values S lying in the range 7000 to 9000, it is possible to select an increment that is relatively coarse (e.g. about 500), since few points lie between these two values in the image under consideration. In contrast, for threshold values S that are greater than 9000, a smaller increment should be selected in order to identify more accurately the gray-scale value that is representative of the real frontier between void and matter (i.e. an increment of the order of 100 or 50).

The porosity ratio $\tau_E$ of the sample E is then obtained by analyzing the variations in the intermediate ratio τ(S) as a function of the threshold values S.

Figure 4:
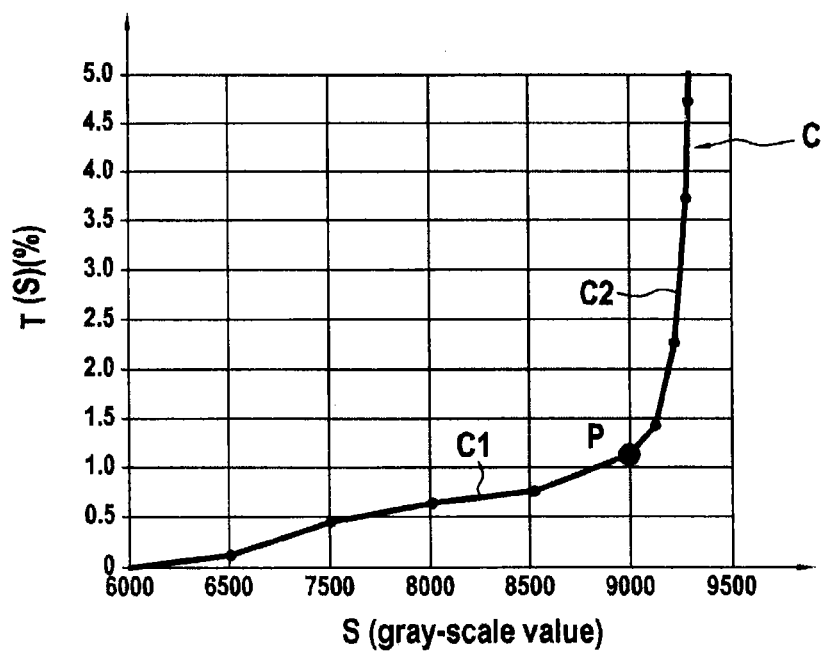
FIG. 4 shows an example of a curve representing the variations of the intermediate ratio as a function of threshold levels.

As mentioned above, the curve C plotting variations in the intermediate ratio as a function of threshold values is very characteristic. An example of such a curve is given in FIG. 4.

As can be seen in this figure, the curve C presents two substantially linear curve portions C1 and C2 of slopes that are very different on either side of a "break" point P. Advantageously, the inventors have observed that the break point P reflecting this significant change of slope in the curve C gives an accurate estimate of the volume porosity ratio $\tau_E$ of the material.

In order to estimate the volume porosity ratio $\tau_E$, the device 1 thus begins by identifying the break point P (step E50).

By definition, the point P corresponds to a maximum in the second derivative of the curve.

Consequently, in the presently described implementation, for each threshold value S, the device 1 evaluates the second derivative of the intermediate ratio τ(S) using conventional means, such as for example with the help of the following approximation:

$$\tau''(S) = \frac{\tau(S - incr) - 2\tau(S) + \tau(S + incr)}{incr \times incr}$$

The values of the second derivative τ''(S) are then stored in the RAM 3 of the device 1 in association with the corresponding threshold values S.

Thereafter, the device 1 searches through the stored values for the maximum value of the second derivative, and extracts the corresponding threshold value, written $S_{max}$. On the basis of this threshold value $S_{max}$, the device 1 obtains the value of the intermediate ratio τ($S_{max}$) stored during step E40 in the RAM 3.

In other words, the coordinates of the break point P are $S_{max}$ and τ($S_{max}$).

The device 1 then estimates the volume porosity ratio $\tau_E$ of the sample E on the basis of the ordinate value of the point (step E60), i.e. in this example:

$$\tau_E = \tau(S_{max})$$

In a variant, if the images are two-dimensional representations of the sample E, the intermediate ratio τ($S_{max}$) is an area ratio. The volume porosity ratio of the sample E can then be obtained by converting this area ratio into a volume ratio, in conventional manner.

In the presently described implementation, the break point is identified by searching for the maximum of the second derivative of the curve C, i.e. of the intermediate ratio. In another implementation, since the curve portions C1 and C2 are practically linear, the break point is obtained by approximating each curve portion with a straight line portion using linear regression, and then finding the point of intersection between the two straight line portions as obtained in this way. Techniques for applying a linear regression to a set of points and for finding the point of intersection of two straight lines are themselves known, so they are not described in greater detail herein. The point of intersection as obtained in this way is then approximated by a point on the curve C (i.e. a search is made for the point on the curve C that is closest to the resulting point of intersection), with the ordinate value of this point constituting an estimate of the volume porosity ratio.

It should be observed that the approach proposed in the invention for estimating the volume porosity ratio of a sample of material E has been validated by the inventors with a matrix dissolving technique. The resulting volume porosity ratios are substantially the same, thus demonstrating the accuracy of the estimation method of the invention (as an indication, during the tests that were performed, an estimate was obtained with accuracy of the order of within 0.1%).

The invention claimed is:

1. An estimation method for estimating a porosity ratio of a sample of material from at least one gray-scale coded image representing the sample, the method comprising:
   evaluating an intermediate ratio for each gray-scale threshold value of a plurality of gray-scale threshold values lying between two determined limit values, the intermediate ratio being equal to a ratio of a number of pixels of the at least one image having a gray-scale value bounded by the gray-scale threshold value to a total number of pixels in the at least one image; and estimating the porosity ratio of the sample by analyzing variations in the intermediate ratio as a function of the threshold value, the estimating the porosity ratio comprising:

identifying, on a curve representing variations in the intermediate ratio as a function of threshold value, a point reflecting a significant change in slope of the curve in which a ratio of slopes on either side of the point is greater than a predetermined threshold; and estimating the porosity ratio of the sample from an ordinate value of the point.

2. An estimation method according to claim 1, wherein the point reflecting a significant change of slope in the curve corresponds to a maximum of the second derivative of the curve.

3. An estimation method according to claim 1, wherein the at least one gray-scale coded image is an image representing the sample in three dimensions, and the estimated porosity ratio is a volume porosity ratio.

4. An estimation method according to claim 3, wherein the at least one gray-scale coded image is obtained by tomography.

5. An estimation method according to claim 1, wherein limit values are determined from information contained in the at least one gray-scale coded image.

6. An estimation method according to claim 1, wherein the material is a composite material.

7. An estimation method according to claim 1, further comprising, prior to the evaluating, classifying the gray-scale values of the at least one gray-scale coded image in increasing or decreasing order.

8. A non-transitory computer readable medium including executable instructions for executing the estimation method according to claim 1 when the instructions are executed by a computer.

9. A device for estimating a porosity ratio of a sample of material from at least one gray-scale coded image representing the sample, the device comprising:

means for evaluating an intermediate ratio for each gray-scale threshold value of a plurality of gray-scale threshold values lying between two determined limit values, the intermediate ratio being equal to a ratio of a number of pixels of the at least one image having a gray-scale value bounded by the gray-scale threshold value to a total number of pixels of the at least one image; and means for estimating the porosity ratio of the sample by analyzing variations in the intermediate ratio as a function of threshold value, the means for estimating:

identifying, on a curve representing variations in the intermediate ratio as a function of threshold value, a point reflecting a significant change of slope in the curve in which a ratio of slopes on either side of the point is greater than a predetermined threshold; and estimating the porosity ratio of the sample from the ordinate value of the point.

* * * * *